United States Patent [19]
Daher et al.

[11] Patent Number: 6,077,540
[45] Date of Patent: Jun. 20, 2000

[54] GELATIN SPRAY COATING

[75] Inventors: Lawrence J. Daher, Elkhart, Ind.;
Thomas P. Callahan, Morristown, N.J.;
Steven M. Lonesky, Monroe City, Pa.

[73] Assignee: Bayer Corporation, Morristown, N.J.

[21] Appl. No.: 08/908,703

[22] Filed: Aug. 8, 1997

[51] Int. Cl.⁷ .................................................. A61K 9/40
[52] U.S. Cl. ........................ 424/478; 424/464; 424/465;
424/474; 424/477
[58] Field of Search .............................. 424/45, 456, 460,
424/463, 474, 475, 466, 478, 464, 465

[56] References Cited

U.S. PATENT DOCUMENTS

| | | |
|---|---|---|
| 4,816,259 | 3/1989 | Matthews et al. . |
| 5,035,896 | 7/1991 | Apfel et al. . |
| 5,104,674 | 4/1992 | Chen et al. . |
| 5,114,720 | 5/1992 | Littell et al. . |
| 5,527,545 | 6/1996 | Santus et al. . |
| 5,603,952 | 2/1997 | Soper . |
| 5,683,717 | 11/1997 | Shen . |

*Primary Examiner*—Thurman K. Page
*Assistant Examiner*—Brian K. Seidleck
*Attorney, Agent, or Firm*—Orrick, Herrington & Sutcliffe LLP

[57] ABSTRACT

This invention provides a coating composition in which the principal film former is gelatin for use in coating tablets. The gelatin coating may be used with tablets, with or without any subcoating, and may be applied using conventional equipment. For a subcoated tablet, the coating formulation contains gelatin, a surfactant and a drying agent.

19 Claims, No Drawings

GELATIN SPRAY COATING

FIELD OF THE INVENTION

The invention is related to spray coating tablets or caplets with an aqueous solution in which the principal film forming ingredient is gelatin.

BACKGROUND OF THE INVENTION

Tablets have been coated in many ways to enhance their market appeal and swallowability. Early coating work generally used sugar solutions. Later polymer coatings, often applied as non-aqueous solutions, were popular, but because of environmental concerns in the United States were generally replaced by water based coatings. After the tamper problems encountered with gelatin capsules, caplets were rounded off more to simulate the shape of a capsule and were coated with gelatin to mimic the appearance of the gelatin capsules. These caplets were coated by dipping into gelatin solutions, as is described in U.S. Pat. No. 4,820,524 and related patents assigned to McNeil; or by enrobing, as is described in U.S. Pat. Nos. 5,146,730 and 5,459,983 assigned to Banner Pharmacaps. Both these techniques required a large capital investment into dedicated equipment. U.S. Pat. No. 5,114,720 discloses spray coating gelatin with a low bloom strength on a precoated tablet or caplet. However, this technique does not appear to have been used as broadly in the pharmaceutical industry as dipping or enrobing techniques, even though it apparently calls for the use of conventional equipment.

SUMMARY OF THE INVENTION

The invention provides a coating composition, a tablet coated with this composition and methods of preparing the coating composition and of coating the tablet.

The coated tablet is composed of a tablet core containing active ingredients and a continuous gelatin coating contributing from about 0.5% to about 5% by weight of the tablet weight. Preferably, colored coatings, will provide a weight gain of from about 2 to about 3.5% by weight of the tablet weight; a clear coating will be in the lower range, preferably providing about 1% weight gain.

The coating composition contains gelatin, a surfactant, a drying agent and water. A plasticizer may be added to the coating composition. Fish or mammalian gelatin may be used. Preferred surfactants are sodium stearoyl lactylate, calcium stearoyl lactylate and glyceryl monostearate. Preferred drying agents are sodium, magnesium or potassium sulfates. Preferred plasticizers, when used, are propylene glycol monostearate and sodium lactate.

A preferred coating composition contains fish gelatin (from about 5 to 25% by weight), sodium stearoyl lactylate, sodium sulfate, propylene glycol monostearate in water. A particularly preferred composition also includes sodium acetate and sodium lactate.

The coating composition may be prepared generally using low shear mixing. It may be advantageous to adjust the pH of the coating composition into the basic range for some uses.

DETAILED DESCRIPTION OF THE PREFERRED EMBODIMENTS OF THE INVENTION

Tablets or caplets of all types may be coated with the composition provided herein with ordinary manufacturing equipment and techniques. However, it is most applicable to the pharmaceutical industry and to the manufacture of medicinal tablets or caplets (referred to generically herein as "tablets"), including acetylsalicylic acid, or of nutritional supplements such as vitamins. Such a coating provides a smooth continuous finish to the tablet, which provides pleasing aesthetics for the consumer, and is also perceived to facilitate swallowing.

Previously it has been difficult to film coat with a water based composition in which gelatin is the major component. The physical properties of gelatin present problems for application with the manufacturing equipment preferred for other types of coating, in particular spray coating in a rotating pan or in fluid bed equipment. This gelatin coating must be distinguished from hard gelatin capsules, from soft gelatin capsules, and from coatings produced by specialized processes such as dipping, enrobing, encapsulating (essentially shrink wrapping a caplet) or coating with a hydrolyzed gelatin (a mammalian gelatin hydrolyzed to provide a low bloom strength). All of these methods suffer from one or more of the following: the requirement of specialized dedicated equipment, high costs and low outputs.

In the past, many tablets have been coated with a light film, for example a hydroxymethyl cellulose film, prior to coating with colored polymeric film which provides the desired aesthetic appearance. This precoating is sometimes referred to as an under or subcoating. Tablets with such light coatings (generally colorless) will be referred to herein as "subcoated" tablets. Subcoats are sometimes also referred to as seal coats by those of skill in the art. For clarity, a tablet core which has not been coated in any way will be referred to as a "raw tablet core" (i.e. not subcoated). In addition, after subcoating and coating, tablets are sometimes subjected to another color coating step and to a third coating step referred to as glossing or "overcoating" herein.

There has been some work with spray coating gelatin previously as disclosed in U.S. Pat. No. 5,114,720. However, the coating formulation disclosed in the '720 patent is based on the use of very low bloom (0 to 80 obtained from hydrolyzed mammalian gelatin). The method provided could only be used with subcoated tablets. The composition provided herein may be used on subcoated tablets, but also may be used on raw tablet cores.

The coating composition of this invention may contain mammalian gelatin of standard bloom strengths. However, fish gelatin, which has an inherent low bloom strength, is preferred since it does not gel at room temperature. Fish gelatin provides preferred compositions for coating raw tablet core's and subcoated tablets.

The negative properties of gelatin that are controlled by the invention disclosed herein are a) its tendency to form cobweb-like filaments upon exiting the spray apparatus, b) its slowness to dry upon deposition on tablet surfaces, and c) its adhesive character during drying which promotes tablet-to-tablet sticking as the sprayed tablets dry while moving past each other in a rotating pan or in fluid bed equipment.

Gelatin forms clear films when deposited from aqueous solutions. If a clear coating is desired, only non-opaque ingredients are included in the coating composition and a coating providing from about 0.5% to about 1.5% tablet weight gain is generally sufficient to provide continuous coverage.

If opaque and/or colored film coated tablets are desired, colorants and opacifiers are to be included in the coating composition to produce the desired effect. Large numbers of such agents are known to those of skill in the art of film coating and suitable ones may be chosen to produce the desired effect. Those of skill in the coating art will appreciate the ranges of alternatives and choices. Certain restrictions will also be appreciated by those of skill in the art. The colorants must be suitable for the particular use. For example FD&C dyes are used for nutritional supplements. In addition, those of skill in the art understand the need to avoid incompatibilities and/or the use of disproportionate quantities of dyes. Generally a continuous coating of an opaque or colored film can be produced with from about 1.5 to about 5% tablet weight gain. Usually from about 2% to about 3.5% weight gain is sufficient to provide a continuous coating and additional coating would simply be a waste of material.

The coating composition of this invention contains gelatin, a drying agent and a surfactant in water. Gelatin is the principal film forming ingredient. Fish gelatin is preferred, but mammalian gelatin having a bloom strength up to 200 has been used with heretofore unachievably good results. Therefore, the invention provided herein may be accomplished with mammalian gelatin of any bloom strength that is generally commercially available and used in the pharmaceutical industry for soft gels and the like.

The surfactant may be chosen from many available in the industry keeping in mind the nutritional/medicinal end product desired. It is believed, but not relied upon, that the adhesive character of gelatin is restrained through the addition of a surfactant which acts to complex the gelatin proteins and such protein complexing surfactants are preferred. Examples of protein complexing surfactants are sodium stearoyl lactylate, calcium stearoyl lactylate and glyceryl monostearate. Others may be chosen by those of ordinary skill in the art of film coating given the guidance and examples provided herein.

Drying agents useful in the coating composition include magnesium aluminum silicate (Veegum) and sodium, magnesium and potassium sulfate. Hydrophilic clays may also be used. The sulfates are preferred and most preferred is sodium sulfate. It is believed, but not relied upon, that the sulfate drying agent may desolvate gelatin and shorten the drying time of the gelatin coating. Magnesium aluminum silicate may act as a detactifying agent. Hydrophilic clays and Veegum are more commonly classified as suspending agents and may play a dual role in these compositions.

A plasticizer may be used in the coating composition and is preferred when coating raw tablet cores. The plasticizer may be chosen from among the large number known to those of skill in the coating art. The plasticizer need only impart temporary softness until the coating is completed (continuous) and the coating on the tablet is dried. Preferred plasticizers are propylene glycol monostearate and sodium lactate; most preferred is propylene glycol monostearate, available from Eastman Chemical Co., (Kingsport, Tenn. 37662 as Myverol P-06).

While gelatin, a drying agent, a surfactant and, optionally, a plasticizer are the primary ingredients in the aqueous coating composition of this invention, other ingredients may be added to provide additional coating properties, such as taste or odor, or to aid in processing. Such additional ingredients include suspending agents, such as magnesium aluminum silicate, leveling agents such as lecithin and phosphated monodiglycerides, sodium, available from Witco, (Chicago Ill. 60638 as Emphos D70-30). Leveling agents have the effect of reducing surface deformities and irregularities in coating materials. A preferred coating composition is composed of gelatin, a drying agent such as sodium sulfate, a protein complexing surfactant such as sodium stearoyl lactylate, a plasticizer such as propylene glycol monostearate, sodium lactate and sodium acetate. Sodium acetate is believed to prevent the reaction of free amine groups in gelatin with sulfonic acid dyes in the composition and therefore prevent the formation of a coacervate.

The coating, as applied, is from about 1 percent to about 5 percent of the final tablet weight. The weight gain of the tablet provided by the coating, after drying, is generally in the range of about 10 to 75 mg.

The coating composition is produced by mixing the ingredients in water. Generally, gelatin and other water soluble ingredients are dissolved in water first and any remaining ingredients are then dispersed in the solution. In the examples given, all the ingredients may be mixed using low shear mixing. Alternatively high shear mixing can be used for all of the ingredients. However, high shear mixing is not preferred since it may produce foaming which may create spraying problems. Generally since a surfactant is included in the composition, high shear mixing is not necessary. Additional details on preferred methods of making the coating composition may be seen in the Examples. With the guidance provided herein, particularly in the Examples, those of skill in the art of coating will be able to vary the method of producing the sing composition to suit particular needs.

Coating may be accomplished with conventional methods in fluid bed equipment or rotating coating pans. It is presently preferred to use the coating solution at room temperature since it appears to give a better gloss to the finished tablets. While the coating composition could be applied by dipping, that method is not a preferred manufacturing method. A preferred method of application is as an atomized spray with fluid bed equipment or a rotating coating pan. Heated air is used in the fluid bed equipment and in the rotating coating pan method to dry the sprayed tablets. It is preferred to spray tablets continuously while the tablets are being dried. Discontinuous or intermittent spraying may be used, but generally requires longer coating cycles and is not preferred.

Unexpectedly, with the coating composition of this invention raw tablet cores may be coated directly. However, the coating composition may be used with subcoated tablets. Gelatin coated tablets by the methods of this invention may be subjected to glossing or overcoating. When overcoating is used it has been found to be advantageous to adjust the pH of the coating composition into the basic range. This pH adjustment may be accomplished in any way feasible. A simple method is to adjust the pH of the aqueous coating solution by the addition of a basic salt such as sodium carbonate, sodium tripolyphosphate or dibasic sodium phosphate. The increase in pH produces a slightly softer coating. This appears to counteract any tendency of the coating to crack in the final product and also to facilitate overcoating if desired.

EXAMPLES

The following components are useful in the coating composition described herein:

| | | |
|---|---|---|
| propylene glycolmonostearate | Myverol P-06 | Eastman Chem. |
| glycerol monooleate | Myverol 18-99 | Eastman Chem. |
| sodium stearoyl lactylate | Emplex | American Ingredient Company |
| glyceryl monostearate | Myvatex SSH | Eastman Chem. |
| magnesium aluminum silicate | Veegum K | RT Vanderbilt Co. Inc. |
| phosphated mono-diglycerides, sodium | Emphos D70-30 | Witco |

Example 1

Gelatin Coating Over a Subcoated Tablet

A subcoating formulation given below was applied to raw tablet cores by conventional spray drying methods.

| subcoating formulation: | |
|---|---|
| ingredients | % w/w |
| lecithin | 0.006 |
| sodium polyphosphate | 0.060 |
| hydroxypropylmethyl cellulose | 6.000 |
| water | 93.934 |
| | 100.00 |

A gelatin coating composition was prepared by dispersing sodium stearoyl lactylate, titanium dioxide, magnesium aluminum silicate (available as Veegum K from RT Vanderbilt Co. Inc. located in Norwalk Conn.), sodium sulfate, and Myvatex SSH with high shear, adding gelatin and mixing further with low shear. The coating composition was sprayed onto the subcoated tablet cores. About 1450 grams were applied in a 24 inch Accela Cota coating pan to a 15 kg batch of capsule shaped tablets.

Example 2

Gelatin Coating of Raw Tablet Cores

| Ingredient | % w/w |
|---|---|
| Sodium Stearoyl Lactylate | .6 |
| Sodium Sulfate | 1. |
| Sodium Polyphosphate | 2.4 |
| Titanium Dioxide | 2.9 |
| Veegum K | .4 |
| Dyes | .9 |
| Myverol P-06 | .7 |
| Emphos D70-30 | .5 |
| Fish Gelatin | 10. |
| Distilled water | 79.55 |
| | 100. |

Myverol, a portion of the sodium stearoyl lactylate (available as Emplex from American Ingredients Company, located in Grandview Md.) and Emphos were melted over low heat and allowed to resolidify. The ingredients were added to and mixed in a Lightin' Mixer. The Myverol/Emphos mixture was added to water heated to 60 degrees Centigrade, and the remaining sodium stearoyl lactylate was added and allowed to disperse. The titanium dioxide and Veegum K then were added and allowed to disperse completely. Gelatin was added and allowed to dissolve completely. All remaining ingredients were added and mixed in the Lightnin' mixer. The coating composition was applied to a nutritional tablet core (raw) using conventional spray coating equipment available in the industry to provide from about 2% to about 2.5% weight gain in the final dried caplet.

Example 3

Gelatin Coating of Raw Tablet Cores

| Ingredient | % w/w |
|---|---|
| Sodium Stearoyl Lactylate | .6 |
| Sodium Sulfate | 1. |
| Sodium Polyphosphate | 2.4 |
| Titanium Dioxide | 2.9 |
| Veegum K | .4 |
| Dyes | .4 |
| Myverol P-06 | .7 |
| Emphos D70-30 | .5 |
| Sodium Acetate | .75 |
| Sodium Lactate (50% solution) | .5 |
| Mammalian Gelatin | 10. |
| Distilled water | 79.93 |
| | 100. |

Generally, the coating composition was prepared as given previously. Mammalian Gelatin (150 bloom strength) was used in place of Fish Gelatin and the sodium acetate and lactate were added with the use of the Lightnin' Mixer. The gelatin coating was applied to a raw nutritional tablet core.

Example 4 pH Adjustment of the Coating Composition

| Ingredient | % w/w |
|---|---|
| Sodium Stearoyl Lactylate | .53 |
| Sodium Sulfate | 1. |
| Sodium Polyphosphate | 2.4 |
| Titanium Dioxide | 2.5 |
| Veegum K | 1.2 |
| Dyes | .34 |
| Myverol P-06/Emplex mixture (90:10) | .79 |
| Myverol 18-99 | .5 |
| Fish Gelatin | 10. |
| Distilled water | 80.73 |
| | 100. |

The coating composition was generally prepared as described previously. However, after most ingredients except the dyes were dispersed or dissolved, sodium carbonate was used to raise the pH of the composition to a pH of 9. The dyes were then added and allowed to dissolve and the composition was stirred and maintained at 60 degrees Centigrade until sprayed. The gelatin coating was applied to a raw nutritional tablet core.

Example 5

A Preferred Formulation

A presently preferred formulation for coating raw tablet cores of a nutritional supplement contains:

| Ingredient | % w/w |
| --- | --- |
| Sodium Stearoyl Lactylate | .53 |
| Sodium Sulfate, Anhydrous | 1. |
| Titanium Dioxide | 2.9 |
| Veegum K | .4 |
| FD & C Yellow #6 | .008 |
| FD & C Yellow #5 | .010 |
| Sodium Stearoyl Lactylate | .8 |
| Myverol P-06 | .7 |
| Emphos D70-30C | .5 |
| Sodium Lactate | 1. |
| Fish Gelatin | 10. |
| Distilled Water | 82. |
| | 100 |

The water is heated to 60 degrees Centigrade. Emplex is added and allowed to disperse completely. The Myverol/Emplex/Emphos Emulsifier is added as a mixture and allowed to disperse. Titanium Dioxide and Veegum K are added and allowed to disperse completely. Gelatin is added and allowed to dissolve completely. The remaining ingredients are added using a Lightnin' Mixer. The coating composition is applied to raw tablet cores to achieve a continuous coating.

Obviously many modifications and variations of the invention as set forth may be made without departing from the spirit or scope of the invention which is defined by the claims herein.

What is claimed is:

1. A tablet comprising:
   a. a subcoated tablet core containing active medicinal or nutritional ingredients; and
   b. a continuous gelatin coating on the subcoated tablet core which coating is composed of gelatin, a surfactant; and a drying agent wherein the drying agent is selected from the group consisting of sodium sulfate, magnesium sulfate and potassium sulfate.

2. A tablet comprising:
   a. a raw tablet core containing active medicinal or nutritional ingredients; and
   b. a continuous gelatin coating on the tablet core which coating is composed of gelatin, a surfactant, a drying agent and a plasticizer wherein the drying agent is selected from the group consisting of sodium sulfate, magnesium sulfate and potassium sulfate.

3. A tablet coating composition comprising:
   a. gelatin;
   b. a surfactant; and
   c. a drying agent wherein the drying agent is selected from the group consisting of sodium sulfate, magnesium sulfate and potassium sulfate.

4. The coating composition of claim 3 in which the gelatin is selected from the group consisting of fish gelatin and mammalian gelatin.

5. The coating composition of claim 4 in which the gelatin is fish gelatin.

6. The coating composition of claim 3 in which the surfactant is a protein complexing surfactant.

7. The coating composition of claim 6 in which the protein complexing surfactant is selected from the group consisting of sodium stearoyl lactylate, calcium stearoyl lactylate and glyceryl monostearate.

8. The coating composition of claim 7 in which the protein complexing surfactant is sodium stearoyl lactylate.

9. The coating composition of claim 3 in which the drying agent is sodium sulfate.

10. The coating composition of claim 3 which additionally includes a plasticizer.

11. The coating composition of claim 10 in which the plasticizer is selected from the group consisting of propylene glycol monostearate and sodium lactate.

12. The coating composition of claim 11 in which the plasticizer is propylene glycol monostearate.

13. The coating composition of claim 10 which additionally includes a leveling agent.

14. A coating composition comprising:
   a. from about 5 to about 25% by weight of gelatin;
   b. a surfactant;
   c. a drying agent selected from the group consisting of sodium sulfate, magnesium sulfate and potassium sulfate;
   d. a plasticizer;
   e. a leveling agent; and
   f. water.

15. The coating composition of claim 14, which is comprised of
   a. from about 8 to 12% by weight of gelatin;
   b. a surfactant selected from the group consisting of sodium stearoyl lactylate, calcium stearoyl lactylate and glyceryl monostearate;
   c. a drying agent selected from the group consisting of sodium sulfate, magnesium sulfate and potassium sulfate;
   d. a plasticizer selected from the group consisting of a propylene glycol monostearate and sodium lactate;
   e. a leveling agent; and
   f. water.

16. The coating composition of claim 15 which additionally includes sodium lactate and sodium acetate.

17. A method of film coating a tablet core, comprising:
   a. spray coating a tablet core with a coating composition containing gelatin, a surfactant, and a drying agent; and
   b. drying the gelatin coated tablet cores wherein the drying agent is selected from the group consisting of sodium sulfate, magnesium sulfate and potassium sulfate.

18. A method of coating a tablet core, comprising the steps of:
   a) forming a water based composition by mixing water, gelatin, a surfactant and a drying agent; and
   b) spraying and drying the water based coating composition on a tablet core to form a continuous coating using equipment wherein the drying agent is selected from the group consisting of sodium sulfate, magnesium sulfate and potassium sulfate.

19. The method of claim 18 in which the water based coating composition is adjusted to a basic pH prior to spraying.

* * * * *

UNITED STATES PATENT AND TRADEMARK OFFICE
CERTIFICATE OF CORRECTION

PATENT NO. : 6,077,540
DATED : June 20, 2000
INVENTOR(S) : Daher, et. al.

It is certified that error appears in the above-identified patent and that said Letters Patent is hereby corrected as shown below:

Column 4, line 34, delete "sing" and insert --coating-- therefor.

Signed and Sealed this

Twenty-second Day of May, 2001

Attest:

NICHOLAS P. GODICI

Attesting Officer   Acting Director of the United States Patent and Trademark Office